United States Patent [19]

Delmas et al.

[11] 4,346,040

[45] Aug. 24, 1982

[54] PROCESS FOR CONVERTING AN ALDEHYDE INTO AN ALKENE, IN PARTICULAR FURFURAL INTO FURFURYLIDENES

[75] Inventors: Michel Delmas, Entraygues; Antoine Gaset, Toulouse; Yves Le Bigot, Saint Martin de Londres, all of France

[73] Assignee: Agrifurane S.A., Bon Encontre, France

[21] Appl. No.: 285,488

[22] Filed: Jul. 21, 1981

[30] Foreign Application Priority Data

Jul. 28, 1980 [FR] France .............................. 80 16767

[51] Int. Cl.³ ............................................. C07D 307/28
[52] U.S. Cl. .................................. 549/505; 568/652; 568/658; 568/939; 585/535; 585/638; 549/506
[58] Field of Search .................. 260/346.11; 568/652, 568/658, 939; 585/435, 638

[56] References Cited

U.S. PATENT DOCUMENTS 4,057,593 11/1977 Bestmann et al. .............. 585/638 X

OTHER PUBLICATIONS

Morrison et al., Organic Chemistry, 1966, Allyn and Bacon, Inc. (Boston) p. 870 and 871.

*Primary Examiner*—Richard Raymond
*Attorney, Agent, or Firm*—Shlesinger, Arkwright, Garvey & Dinsmore

[57] ABSTRACT

The invention relates to a process for converting an aldehyde into a corresponding alkene and of the type wherein the aldehyde is placed in the presence of a phosphoric reagent and a base in solution in an organic aprotic solvent; the process comprising using a mineral base evincing in an aqueous medium a basic force less than or equal to that of the hydroxide ion or a strongly basic organic base of the nitrogen compounds family and adjusting the hydration rate of the reaction medium in such a manner that there are about 0.5 to 5 moles of water per mole of aldehyde.

11 Claims, No Drawings

PROCESS FOR CONVERTING AN ALDEHYDE INTO AN ALKENE, IN PARTICULAR FURFURAL INTO FURFURYLIDENES

The invention concerns a process for converting an aldehyde into a corresponding alkene. It applies particularly to the conversion of furfural into furfurylidenes that are various substituted. The term aldehyde means in a general way any substance with one or several aldehyde functions.

The WITTIG reaction which was discovered in 1954, is much used presently to prepare alkenes from corresponding aldehydes; this reaction in particular allows obtaining alkenes which have been functionalized (substituted) or not in the alpha or beta position to a carbon of the ethylenic double bond by means of a cycle or an aliphatic chain, and unfunctionalized at the same carbon by a heteroatom or a heteroatomic functional group. It is known that this type of alkenes intervenes in many syntheses or they themselves are directly active in many fields, namely in chemical engineering (polymers, synthesis intermediates...), in pharmaceuticals (antibacterial or analgesic substances...), the chemistry of agriculture and of foodstuffs (pheromones, perfumes, insecticides and so forth). The furfurylidenes are particularly active in the latter field, essentially on account of their antibacterial and antifungal properties.

The WITTIG reaction consists in a condensation of a phosphonium salt and a carbonylated compound in the presence of certain strong bases in a strictly anhydrous medium. The bases used are strong bases of the butyllithium hydride type which decompose water (the basic strength exceeds that of the hydroxide ion).

On an industrial scale, the production of alkenes by this reaction raises technical problems which are quite difficult to overcome. In the first place, the strictly anhydrous state of the reaction medium is difficult to achieve in industrial plants and requires treatments and special implementation controls which are very costly (drying by ovens, nitrogen flow, etc.). Moreover the strong bases used react violently and explosively with water, whereby their storage is dangerous. Again these products are expensive and substantially burden the cost of the synthesis. Further, the reaction as a rule is initiated in heavy solvents (such as dimethyl sufloxide (DMSO), dimethyl formamide (DMF), hexamethyl phosphorotriamide (HMPT) which are difficult to separate from the reaction products and to recycle. Lastly this reaction—of which the yield is satisfactory with the aromatic aldehydes—, become of little interest with the aliphatic aldehydes due to the low yields.

In order to eliminate or reduce these drawbacks, many studies and two basic types of implementation have been developed regarding the WITTIG reaction. One of these techniques, applied to the WITTIG reaction about 1975, is the phase transfer catalysis (described in TETRAHEDRON LETTERS #30, 1974, PERGAMON PRESS, UK, W. Tagaki et al). This technique permits averting the drawbacks relating to the anhydrous state imposed on the medium, but entails the presence of a substantial and corrosive aqueous phase whereby the significance of the technique is restricted. Moreover the alkene yield is mediocre and the reaction is not stereo-selective (the Z/E ratio is of the order of unity). Lastly this technique does not apply to the aliphatic aldehydes due to the secondary aldolization reactions taking place. This restriction is a serious practical drawback because the aliphatic alkenes are extremely useful substrates indispensable for the synthesis of active products that are essential in biochemistry, for instance the pheromones and the prostaglandins.

Another technique makes use of a so-called WITTIGHORNER reaction, derived from the WITTIG reaction, and consists in reacting a phosphonate in the presence of a strong phase in a diphasic liquid medium consisting of an aqueous phase and an organic phase (see for instance SYNTHESIS periodical, 1976, 396, M. Mikolajczyk et al). A variation described in 1979 (SYNTHESIS periodical, 1979, 884 Foucauld et al) consists in performing the reaction in liquid/solid phases. However, like the previous technique and for the same reasons, this technique in inapplicable to the aliphatic aldehydes and this represents a serious restriction, as already mentioned. Moreover, the implemented reaction, which is possible only for a phosphonate (and not a phosphonium salt,—essentially allows obtaining alkenes which are functionalized in alpha or beta position of the carbon of the ethylenic double bond from the phosphonates in a heteroatom or a heteroatomic functional group. These alkenes differ very much with respect to their activity from those cited above.

It is the object of the present invention to provide a novel process for converting an aldehyde into an alkene of the type wherein the aldehyde is placed in the presence of a phosphoric reagent and a base in solution in an aprotic organic solvent.

The object of the invention is to provide a process permitting production of an alkene substituted or unsubstituted at the $\alpha$ or $\beta$ position, the $\alpha$ position being the ethylenic carbon furnished by the phosphoric reagent, by a cyclic or aliphatic chain, and not substituted starting from the same carbon by a heteroatom or a heteroatomic functional group.

In particular an object of this invention is to provide a process of this type, which may be implemented at satisfactory yields both with aromatic or heteroaromatic aldehydes and aliphatic aldehydes to obtain the above cited type of alkenes.

Another object is to eliminate the rigorous requirement of the anhydrous character of the WITTIG reaction by providing a process which can be carried out in the presence of water under high-performance conditions.

Another object is to permit the use of conventional bases presenting no danger at all and enjoying low costs.

Another object of the invention is to provide a process capable of employing a light-weight solvent of low cost and amenable to regeneration, and where the synthesis products can be easily separated.

Another object is to provide a process implementing a non-exothermic reaction without any danger, even in the presence of large product quantities, and taking place under moderate temperature and pressure conditions.

Another object is to provide such a process resulting in good stereo-selectivity.

To that end, the converison process object of the invention is of the type wherein an aldehyde is placed in in the presence of a phosphonium salt and a base in solution in an aprotic organic solvent. In conformity with the present invention the production of an alkene substituted or unsubstituted at the $\alpha$ or $\beta$ position, the $\alpha$ position being the ethylenic carbon furnished by the phosphoric reagent, by a cyclic or aliphatic chain, and not substituted starting from the same carbon by a heteroatom or a heteroatomic functional group takes place under the following conditions:

a mineral base which is an aqueous medium evinces a basic force less than or equal to that of the hydroxide ion, or a strongly basic organic base of the family of the nitrogen compounds, in particular pyridine and triethylamine, is used;

the hydration rate of the organic reaction medium is so adjusted that there are about 0.5 to 5 moles of water per mole of aldehyde in this medium.

Thus the originality of this conversion process of the invention is the fact that the conversion reaction of the aldehydes takes place with a phosphonium salt in an organic medium at a low hydration rate which is accurately controlled.

It is mandatory to note that the aldehyde, the phosphoric reagent and also the base are not in an aqueous solutions. Where a mineral base is concerned, it is in the solid state, the aldehyde and the phosphonium salt being in solution in the organic solvent. In the case of an organic base from the amine family, the three substances are in solution in the organic solvent. Thus in any event there is a single organic liquid phase at a low and controlled hydration rate.

Experiments have shown that control of this hydration rate within the above defined range and using a base from the stated group allow very high-yield selective conversions of aldehyde into alkene. This hydration rate is easily controlled and thus the difficult conditions of the WITTIG reaction are eliminated. This hydration rate can be preferentially adjusted to be roughly 2 moles of water per mole of aldehyde, this rate resulting clearly in a maximum yield.

Moreover the base used may be a conventional base, in particular an ionic potassium compound where the anion is of a basic character (potassium hydroxide, potassium carbonate, potassium phosphate, potassium perchlorate...). This kind of base holds no danger at all in industry and its cost is low.

Also, it has been observed that this reaction provides good yields with aliphatic aldehydes, whether functinalized or not. The process conditions permit the inhibition of the secondary aldolization reactions, which explains that the yields obtained from this type of aldehyde also are high.

It should be noted that for the case of the aromatic aldehydes, there sometimes take place—for the conventional reactions—side reactions (CANNIZARO side reactions) restricting the alkene yield. As regards the process of the invention, this reaction is hardly detectable at all, and it is wholly inhibited when potassium carbonate is used as the base.

The reaction of the process of the invention is slightly endothermic and causes no danger at all of abrupt changes. The yield is improved by heating slightly. In practice, the reaction medium preferably is raised to a temperature approximately between 40° and 110° C.

The solvents used advantageously are non-basic or only slightly basic organic solvents such as dioxane, dimethoxyethane (DME), methylene chloride. These solvents generally improve the reaction yield and allow easy separation of the alkenes by distillation. They are low-cost and very easily regenerated.

Certain solvents such as the oxygenated or aromatic solvents result in a very stereo-selective reaction, the Z alkene being obtained perdominantly. Other solvents such as methylene chloride result in a non-stereoselective reaction, whereby the process of the invention allows orienting the stereo-chemistry of the reaction as a function of the particular application by suitably choosing the solvent.

Moreover it has been observed that the yield can be increased by so adjusting the amount of solvent as to obtain an aldehyde dilution between about 0.2 and 2 moles per liter of solvent.

Again, regarding the relative product proportions, the following conditions are advantageous observed: the base used is in a slight stoichiometric excess over the aldehyde, and the phosphonium salt used is in a slight stoichiometric excess over the aldehyde.

For the frequent case where it is desired to produce an alkene which is not substituted at the alpha or beta position to the ethylenic double bond, the $\alpha$ position being the carbon obtained from the phosphonium salt, preferably a phosphonium salt obtained from triphenylphosphine and a R CH$_2$X halide will be used, where X is a halide ion (Cl, Br, I) and R may be an aliphatic chain, substituted or not, or a saturated or unsaturated cyclic compound substituted or not. These alkenes are of practical interest, widely and variously, in chemical agriculture, in pharmaceuticals, in the chemical industry, both as regards their biological activities proper and synthesis intermediary products. A great advantage of the invention is to allow orienting the reaction toward this kind of compound.

The invention which was described in a general way above will now be illustrated below by non-restricting, implementing examples.

EXAMPLE 1

Vinyl-2-furan is synthesized from furan carboxaldehyde-2 in the presence of potassium carbonate and methyltriphenyl phosphonium bromide in nitrobenzene.

0.025 moles of phosphonium salt, 0.025 moles of potassium carbonate, 0.02 moles of aldehyde and 0.04 moles of water in 20 cm$^3$ of nitrobenzene are placed in a 250 ml reactor provided with a coolant, a mechanical agitator and an adding funnel.

The solution is gradually heated to 90° C. for 6 hours. The reaction mixture then is cooled to the ambient temperature. The major part of the triphenylphosphine oxide formed precipitates and is separated by filtering off the organic phase which thereafter is analyzed by vapor phase chromatography in a column of the OV101 type. After the liquid organic phase is dried in magnesium sulfate, the vinyl 2-furan formed is obtained at a nearly 90% yield following distillation. The solvent then is recovered and recycled.

Vinyl-2-furan is characterized by its infrared and nuclear-magnetic-resonance (NMR) spectra of the proton and of carbon 13, the results of which are confirmed by microanalysis.

The initial compound, namely furan carboxaldehyde-2 (or furfural) is produced industrially starting from agricultural secondary products rich in pentosanes (maize stalks, rice and oat chaff, canetrash, peanut shells and wood wastes). These wastes treated in a concentrated acid medium result in aldopentoses obtained by hydrolyzing their pentosanes which dehydrate to end up as furfural.

EXAMPLE 2

Pentene-1, yl-2 furan is synthesized from furan carboxaldehyde-2 in the presence of potassium carbonate and butyltriphenyl phosphonium bromide in dimethoxy-1,2-ethane.

0.025 moles of phosphonium salt, 0.025 moles of potassium carbonate, 0.02 moles of aldehyde and 0.04 moles of water in 20 cm$^3$ of dimethoxy-1,2-ethane are placed in an identical 250 ml reactor.

The medium is agitated either
for 3 hours at reflux
or 6 hours at 80° C.
or 12 hours at 60° C.

These conditions permit the conversion of furfural into furfurylidene-2-butane which is extracted following filtration, drying and concentration of the reaction medium by chromatography on a short silica gel column using hexane as the elutrient.

EXAMPLE 3

Hydroxy-1, methoxy-2, pentene-1,yl-4 benzene is synthesized from vanillin in the presence of potassium carbonate and butyl-triphenyl phosphonium bromide in dioxane-1,4.

0.12 moles of phosphonium salt, 0.12 moles of potassium carbonate, 0.1 moles of aldehyde and 0.2 moles of water in 100 cm$^3$ of dioxane-1,4 are placed in a 1-liter reactor.

After 6 hours of reflux reaction of the dioxane-1,4 the reaction medium is filtered, dried and concentrated. The alkene formed is obtained after distillation (boiling point: 90° C. at 0.5 mm Hg) with a yield near 70% and is characterized by its infrared and NMR spectra.

The reaction is stereo-selective and the Z isomer is predominant (% isomer E/% isomer Z=85/15).

The phenol aldehydes which thus can be made valuable for the most part are extracted from vegetal matters by biologically or chemically treating lignin.

EXAMPLE 4

Anethole is synthesized starting from anisaldehyde in the presence of potassium carbonate and ethyle triphenyl phosphonium bromide in dioxane-1,4.

0.025 moles of phosphonium salt, 0.025 moles of potassium carbonate, 0.02 moles of aldehyde and 0.04 moles of water in 20 cm$^3$ of dioxane-1,4 are mixed in a reactor.

The reaction mixture is agitated with reflux of the dioxane-1,4 for two hours. The anethole (% isomer Z/% isomer E-87/12) is obtained in pure form with a yield of about 85% and is identified by comparison with the commercial product and by its infrared and NMR spectra.

EXAMPLE 5

Pentene-1,yl-1 benzene is synthesized from benzaldehyde in the presence of sodium hydroxide and butyl-triphenyl phosphonium chloride in methylene chloride.

0.025 moles of phosphonium salt, 0.025 moles of sodium hydroxide, 0.02 moles of aldehyde and 0.04 moles of water in 20 cm$^3$ of methylene chloride are placed in a reactor.

After 2 hours' reaction with solvent reflux, the alkene is obtained in pure form with a yield of 90% determined after extraction from the medium by column chromatography. The reaction in the methylene chloride no longer is stereo-specific (% isomer Z/% isomer E-50/50).

EXAMPLE 6

Divinylbenzene is synthesized from terephthalic aldehyde in the presence of potassium carbonate and methytriphenyl phosphonium in dioxane-1,4.

0.05 moles of phosphonium salt, 0.5 moles of potassium carbonate, 0.02 moles of aldehyde and 0.1 moles of water in 30 cm$^3$ of dioxane-1,4 are mixed in a reactor.

The reaction medium is agitated with reflux of the dioxane-1,4 for 2 hours. The divinylbenzene is obtained with a yield of 85% and is identified by comparison of its physical-chemical properties with those of the commercial product.

EXAMPLE 7

Decene-5 is synthesized from hexanal in the presence of potassium carbonate and butyl-triphenyl phosphonium bromide in dioxane-1,4.

0.025 moles of phosphonium salt, 0.025 moles of potassium carbonate, 0.02 moles aldehyde and 0.04 moles of water in 20 cm$^3$ of dioxane-1,4 are mixed in a reactor.

The reaction mixture is made to reflux and agitated for 4 hours. The decene-5 is obtained following column chromatography with a yield of 80% and identified and characterized by comparison with the commercial product.

It must be emphasized that the aldolization sidereaction is inhibited for these experimental conditions.

EXAMPLE 8

A pheromone of the "diptera musca domestica" insect is synthesized from octanal and pentadecanyl-triphenyl phosphonium bromide in the presence of potassium carbonate in dioxane-1,4.

0.025 moles of phosphonium salt, 0.025 moles of potassium carbonate, 0.02 moles of aldehyde and 0.04 moles of water in 20 cm$^3$ of dioxane-1,4, are mixed in a reactor.

The reaction medium is made to reflux and kept agitated for 10 hours. The corresponding alkene is obtained following column chromatography with a yield of 70% and is characterized by its infrared and nuclear magnetic resonance spectra and by microanalysis.

In this manner a great many pheromones can be obtained. Illustratively, using myristic aldehyde and the same phosphonium salt, a "diptera-musca automnalis" insect phoromone is obtained.

EXAMPLE 9

P-nitrostyrene is synthesized from polymerized formaldehyde and p-nitrophenyl-triphenyl phosphonium bromide in the presence of potassium carbonate in dioxane-1,4.

0.025 moles of phosphonium salt, 0.025 moles of potassium carbonate, 0.02 moles of (trioxane or paraformaldehyde) formaldehyde and 0.04 moles of water in 20 ml of dioxane-1,4 are placed in a 250 ml reactor.

Following two hours' reaction at 80° C., the reaction medium is cooled to the ambient temperature, filtered, dried on magnesium sulfate. Then the concentrated solution is made to trickle in the presence of hexane as the elutrient in a short silica gel column. The p-nitrostyrene (melting point 29° C.) is obtained pure with a yield of 90%.

It must be noted that for all these examples, the increase in the amount of the base does not significantly alter the reactivity, probably indicating that the water tends to enhance the decomposition of the intermediary adduct.

While this invention has been described as having a preferred design, it will be understood that it is capable of further modification. This application, is therefore, intended to cover any variations, uses, or adaptations of the invention following the general principles thereof and including such departures from the present disclosure as come within known or customary practice in the art to which this invention pertains, and as may be applied to the essential features hereinbefore set forth and fall within the scope of this invention or the limits of the claims.

We claim:

1. In a process for converting an aldehyde into a corresponding alkene, wherein the aldehyde is placed in the presence of a phosphonium salt and a base in the solution of an aprotic organic solvent, for obtaining an alkene substituted or not in alpha or beta of the carbon of the ethylenic double bond obtained from the phosphonium salt by a cyclic or an aliphatic chain and not substituted from the same carbon by a heteroatom or a heteroatomic functional group, the improvement comprising using as said base a compound selected from the group consisting of (i) mineral bases which in aqueous medium produce a basic strength less than or equal to the basic strength of the hydroxide ion and (ii) organic bases of the nitrogen compound family, and adjusting the hydration rate of the organic reaction medium so as to provide approximately 0.5 to 5 moles of water per mole of aldehyde in the reaction medium.

2. A conversion process as in claim 1, characterized in that the hydration rate of the reaction medium is adjusted to provide about 2 moles of water per mole of aldehyde.

3. A conversion process as in claim 1, characterized in that said base comprises a potassium ion compound where the anion is of a basic character when appropriate water is added in order to achieve the above cited hydration rate.

4. A conversion process as in claim 3, characterized in that said base is in slight stoichiometric excess of the aldehyde.

5. A conversion process as in claims 1, 2, 3 or 4, characterized in that the reaction is carried out in solution in a non-basic or only slightly basic organic solvent.

6. A conversion process as in claim 5, characterized in that said solvent is selected from the group consisting of dioxane, dimethoxyethane (DME), methylene chloride and nitrobenzene.

7. A conversion process as in claim 5, and including adjusting the amount of the solvent so as to achieve an aldehyde dilution between about 0.2 and 2 moles per liter of solvent.

8. A conversion process as in claim 7 for obtaining an alkene unsubstituted in alpha or beta position to the ethylenic double bond, characterized by using as the phosphonium salt a salt obtained from triphenyl phosphine and a halide $R\ CH_2\ X$ where X is a halide ion (Cl, Br, I) and R is a substituted or unsubstituted aliphatic chain, or a saturated or unsaturated substituted or unsubstituted cyclic group.

9. A conversion process as in claim 1 wherein the phosphonium salt is in a slight stoichiometric excess over the aldehyde.

10. A conversion process as in claim 1, 3 or 4 and including heating the reaction medium to a temperature of approximately between 40° C. and 110° C.

11. A conversion process as in claim 10, for the conversion of furfural into variously substituted furfurylidenes, characterized in that the base used in $K_2CO_3$ and the solvent is selected from the group consisting of dioxane and nitorbenzene.

* * * * *